United States Patent [19]
DeBellis

[11] Patent Number: 5,496,354
[45] Date of Patent: Mar. 5, 1996

[54] PACEMAKERS TO ALLOW SAFE AND QUICK REPLACEMENT WITHOUT INTERRUPTING THE ELECTRIC STIMULATION OF THE HEART

[75] Inventor: Ferruccio DeBellis, Rome, Italy

[73] Assignee: P.A.&M. S.p.A., Italy

[21] Appl. No.: 161,665

[22] Filed: Dec. 3, 1993

[30] Foreign Application Priority Data

Dec. 11, 1992 [IT] Italy ................... RM92A0891

[51] Int. Cl.⁶ ............................................. A61N 1/36
[52] U.S. Cl. ............................................. 607/37
[58] Field of Search ........................... 607/9, 36, 37

[56] References Cited

U.S. PATENT DOCUMENTS 4,774,951  10/1988  Osypka ........................... 607/37

FOREIGN PATENT DOCUMENTS

3718826  12/1988  Germany ........................... 607/37

Primary Examiner—William E. Kamm
Assistant Examiner—Marianne Parker
Attorney, Agent, or Firm—DeLio & Peterson

[57] ABSTRACT

Improvement in pacemakers for a quick and safe replacement thereof without interrupting the electric stimulation of the patient's heart from the outside, wherein the contact pin of the electro-de-catheter inserted in the pacemaker is accessible from the outside, and related tool to be utilized therewith by which tool the contact pin can be pushed out of the pacemaker; the tool is provided with contact means to the electrode catheter which means make it possible the uninterrupted electric stimulation of the heart during the whole replacement operation of the pacemaker.

8 Claims, 10 Drawing Sheets

PACEMAKERS TO ALLOW SAFE AND QUICK REPLACEMENT WITHOUT INTERRUPTING THE ELECTRIC STIMULATION OF THE HEART

This invention relates to an improvement in pacemakers as it allows safe and quick replacement thereof without interrupting the electric stimulation of the heart which stimulation is provided for by an external pacemaker during the entire replacement operation.

As known to persons skilled in the art, the replacement operation of an exhausted pacemaker or a pacemaker that in some way is unable to perform its functions has, at present, two main drawbacks, namely a functional and a mechanical drawback.

The functional drawback is the practically inevitable interruption of electric stimulation of the heart in all cases where the electrode-catheter is not equipped with a radiofrequency receiver for an emergency stimulation from the outside.

The mechanical drawback is the difficulty that may be encountered in trying to remove the contact-pin of the electrode-catheter from the PM being replaced.

At present, once the locking screw has been unscrewed, the contact-pin is removed by a traction applied on the electrode; when acting this way there is a high risk of the electrode-catheter being damaged beyond repair, especially when a bipolar or multipolar-electrode-catheter is implanted.

The invention overcomes the aforementioned drawbacks both by providing a structural modification of the pacemaker and making use of a tool specifically designed to allow the easy and quick extraction of the contact-pin without risks of damaging the electrode-catheter, at the same time, keeping uninterrupted, the electric stimulation of the patient's heart by means of an external pacemaker.

The modification of the pacemaker consists in providing, in the pacemaker body, a passageway that gives access from the outside to the contact-pin of the electrode-catheter in order to allow the same to be pushed out of its seat, once the locking screw is unscrewed.

This is achieved by making use of a tool specifically designed to exert a pushing action on the contact-pin through the open passage.

The tool is also equipped with an internal, so called, "mandrel" or conducting wire that, during the entire expulsion, is in contact with the electrode-catheter which, in turn, remains in contact with the patient's heart.

By connecting the conducting wire to an external pacemaker by suitable clamps, the stimulation of the patient's heart during replacement of the exhausted pacemaker is continuously assured by a new efficient pacemaker.

The invention is now described in more details with reference to the attached drawings wherein.

Figure 1:
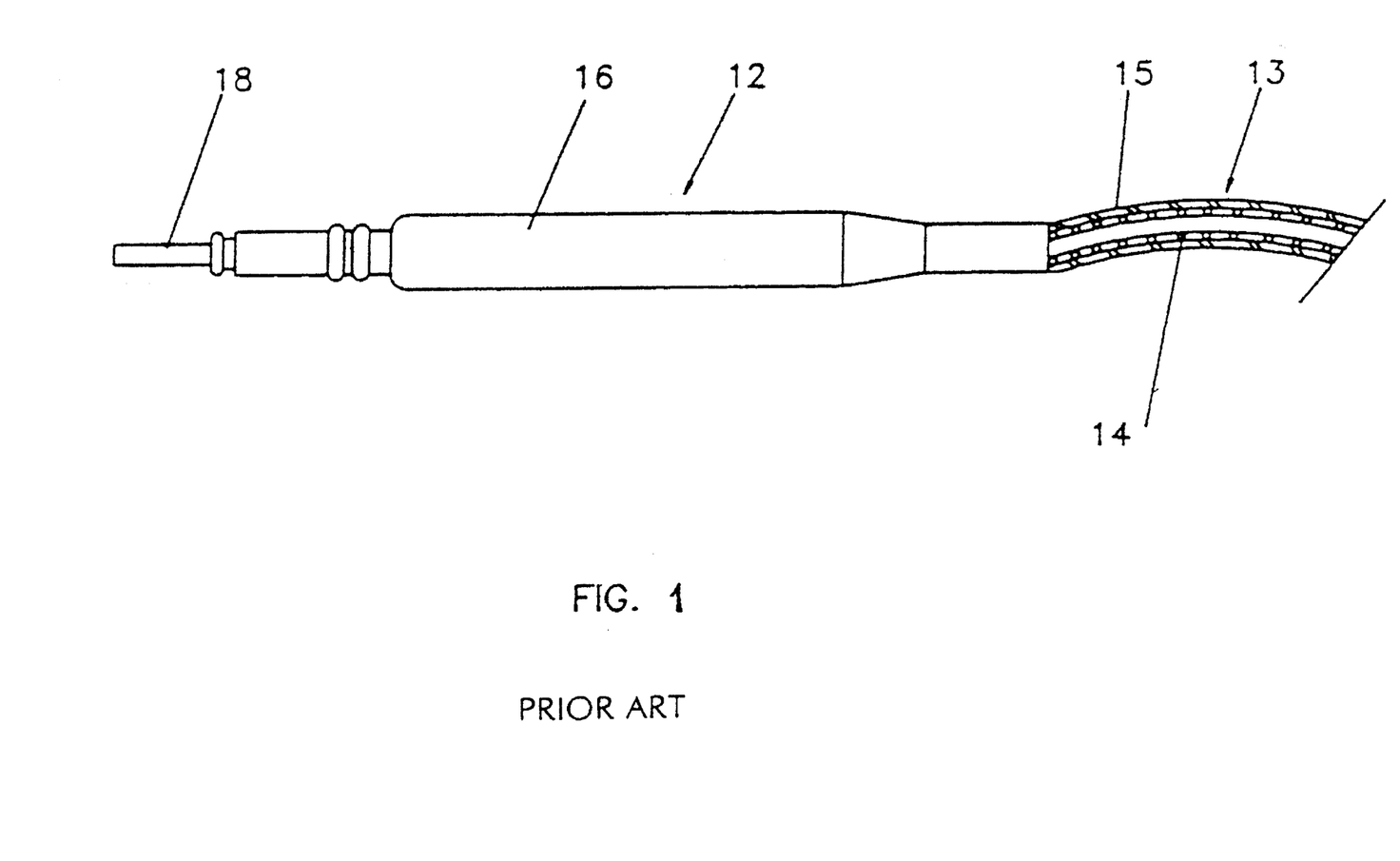
FIG. 1 shows part of the distal end of the electrode-catheter used for cardiac stimulation, including the contact-pin of the type currently used in pacemakers.
Figure 2:
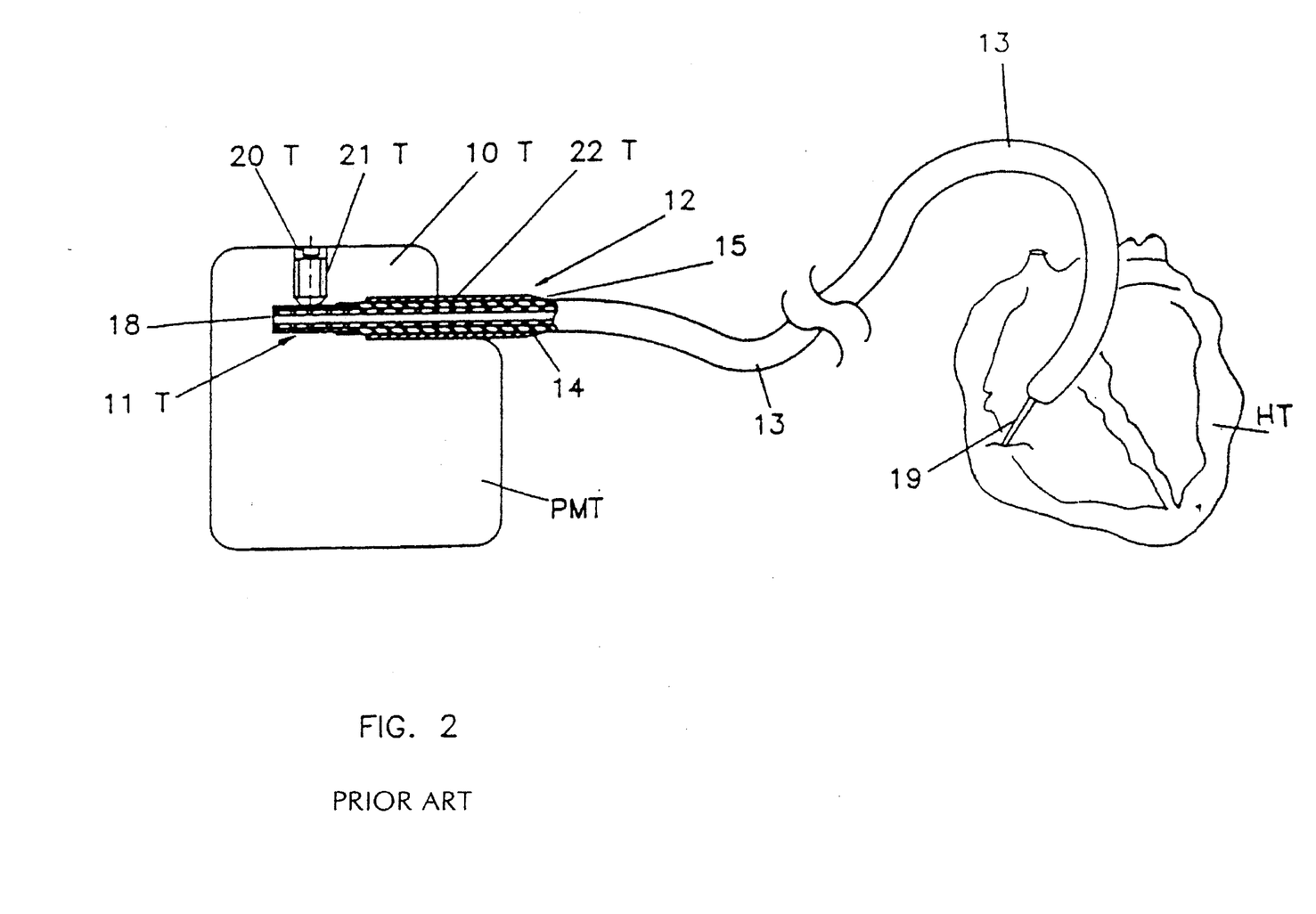
FIG. 2 shows schematically the section of the top portion of a traditional pacemaker to which the electrode-catheter of FIG. 1 is connected.

Looking at FIGS. 1 and 2, the end of an electrode-catheter is shown for the electric stimulation of the heart, or cardiac assisted stimulation, of the type currently used including the distal end of electrode-catheter 13, equipped with the contact-pin 12 for the connection to the pacemaker.

Figure 3:
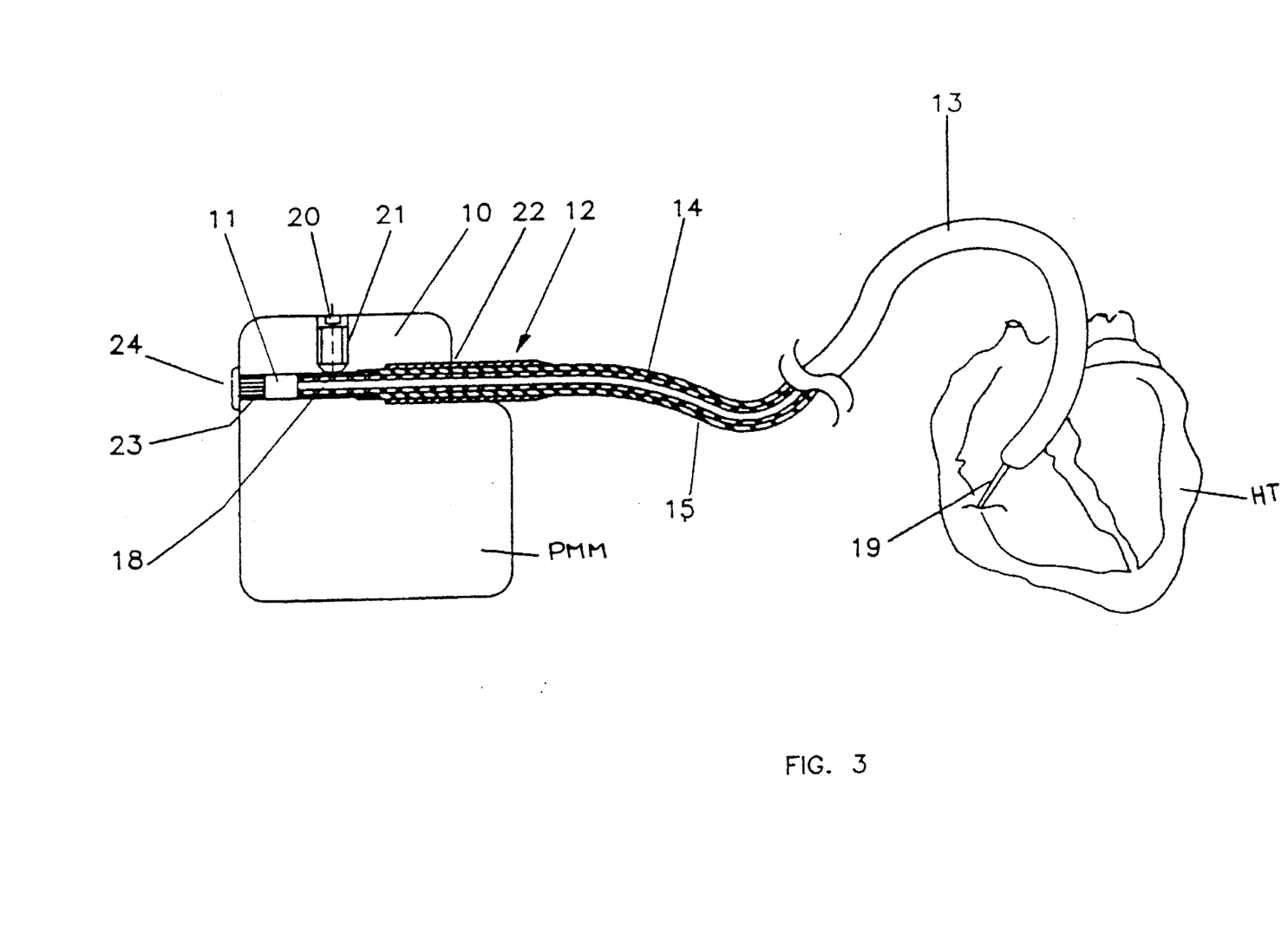
FIG. 3 is a section similar to that of FIG. 2 of a pacemaker modified according to the invention, to which the electrode-catheter of FIG. 1 is connected.

As known, the electrode-catheter 13 comprises a flexible hollow spiral 14 made of special alloy and coated with an insulating sheath while contact-pin 12 comprises an enlarged section 16 and a small metal contact tube 18 protecting the end of spiral 14 and electrically in contact therewith, being the other end 19 of said spiral 14 inserted in the right ventricle of heart HT to be stimulated (FIGS. 2 and 3).

FIG. 2 shows a traditional pacemaker PMT and its top portion 10, where seat 11T is located, in which contact-pin 12 of FIG. 1 is fitted and contact tube 18 is locked by locking screw 20 screwed in its threaded seat 21, to establish a firm electric contact between the operating portion of the pacemaker PMT, not shown, and electrode-catheter As mentioned, distal end 19 of electrode-catheter 13 is inserted in the patient's heart HT.

As known to persons skilled in the art, electrode-catheter 13 can be of the unipolar or multipolar type as required according to the functions that pacemaker PMT is capable of performing being the invention indifferently applicable to electrode-catheters of all type.

As shown in FIG. 2, in the pacemaker of the traditional type, seat 11T, wherein contact-pin 12 of electrode-catheter is fitted and connected, is a passage closed at one end, that is, seat 11T is a blind bore.

With this construction the removal of contact-pin 12 from its seat can be obtained only by gripping the terminal portion of electrode-catheter 13 close to contact-pin 12 and exerting a more or less energetic traction, once screw 20 is unscrewed.

As known to experts, this traction has always a damaging effect and, in the case of a multipolar electrode, may cause damage beyond any possible repair of the electrode.

According to the invention, the seat formed in the modified pacemaker, referred to by reference PMM, is of the "pass-through" type as it completely perforates top portion 10 of the pacemaker.

In this way seat 11 has, on one side, a chamfered access 22 in which contact-pin 12 is fitted and, on the other side, an opening 23 which is normally sealed with a "grommet" or plug 24.

As shown, in the top portion of pacemaker PMM a threaded seat 21 is similarly provided in which locking and contact screw 20 is located.

For the rest, modified pacemaker PMM is identical with a traditional pacemaker PMT.

Figure 4:
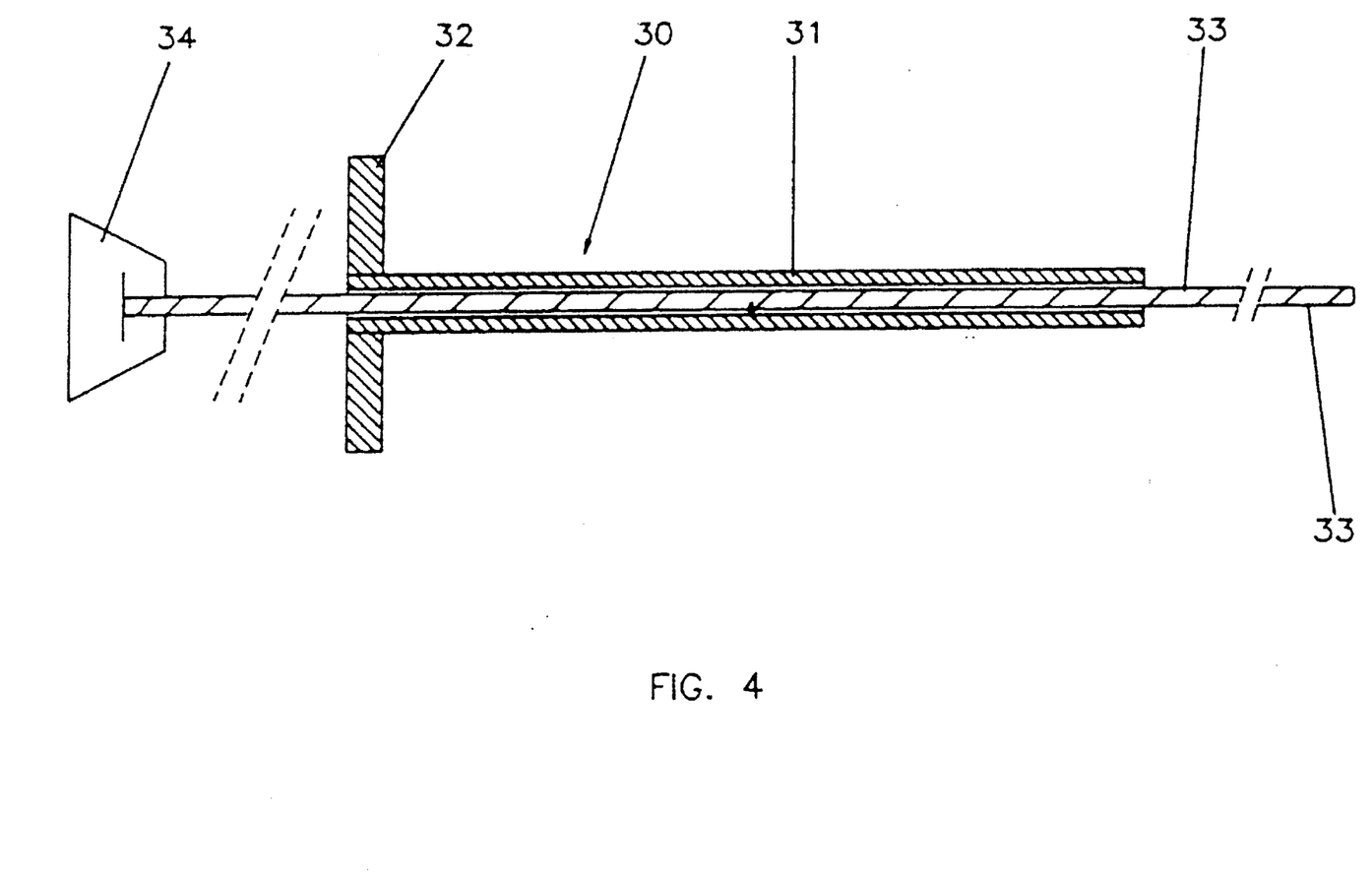
FIG. 4 is a section of the tool of the invention, complete of the conducting wire or "mandrel"

In FIG. 4 the tool according to the invention is shown, indicated by reference number 30.

Tool 30 comprises a cylindrical hollow body 31 with head 32 and the "mandrel" or conducting wire 33, of high mechanical strength and flexibility; conducting wire 33 is much-longer than cylindrical body 31 and is provided with an operating head 34.

Body 31 of the tool has the same diameter of metal contact tube 18 of contact-pin 12 of electrode-catheter 13 and can easily be fitted in seat 11 of the contact-pin 12 through opening 23, once plug 24 is removed.

Conducting wire 33 has such a diameter to pass through hollow cylindrical body 31 and be inserted in contact tube 18 and subsequently inside spiral 14 in order to establish an optimal electric contact therewith.

With the various parts made and assembled as described, use of tool 30, in the modified pacemaker PMM being replaced, is very simple.

After pocket TST in the patient's chest has been opened, which pocket accomodates the pacemaker to be replaced (FIG. 7), "grommet" or plug 24 is removed from opening 23 and, without unscrewing locking screw 20, tool 30 is fitted in seat 11 until it rests against end 27 of contact tube 18 of contact-pin 12.

Figure 5:
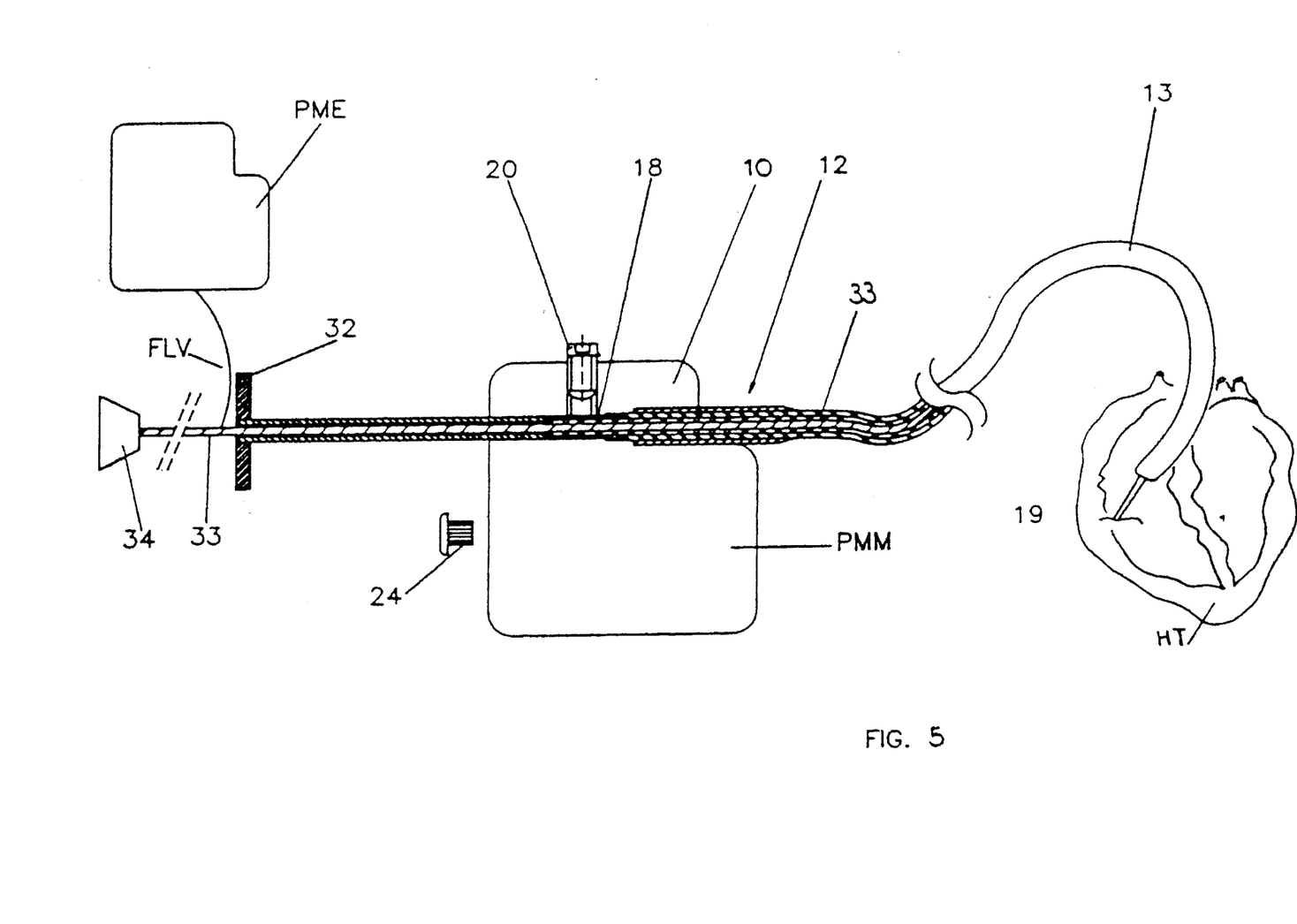
FIG. 5 is a section similar to that of FIG. 4, showing the modified pacemaker with the tool in operating position for the expulsion of the contact-pin from the pacemaker and the internal wire connected to the electrode-catheter.
Figure 7:
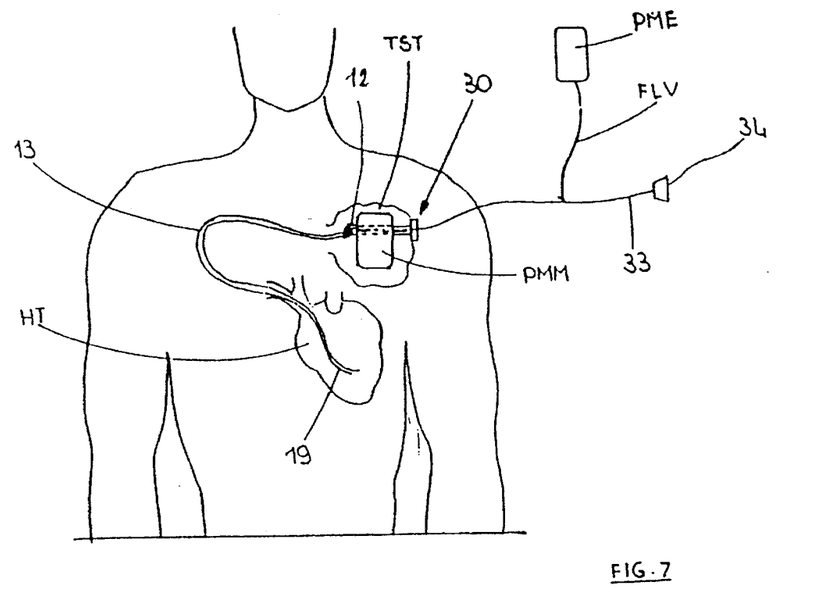
FIGS. 7 and 8 show schematically the removal of the pacemaker following the operations shown in FIGS. 5 and 6 and the necessary connections with the external pacemaker to avoid any interruption of the electric stimulation of the heart.

Conducting wire 33 is then fitted in the bore of cylindrical body 31 of the tool gripping the end equipped with head 32 and pushed therethrough until it exits at the other side and deeply penetrates the bore of spiral 14, at which point conducting wire 33 is connected to external pacemaker PME by means of a temporary connection FLV, outside the pacemaker PMM being replaced (FIGS. 5 and 7).

Locking screw 20 is then unscrewed and tool 30 is further pushed through passage 23 in order to expel, out of cavity 22, contact-pin 12 while the same is sliding along conducting wire 33.

It is important to remind that the stimulation of heart HT, at this point, is provided for by external pacemaker PME via temporary connection FLV, conducting wire 33 and electrode-catheter 13.

Figure 6:
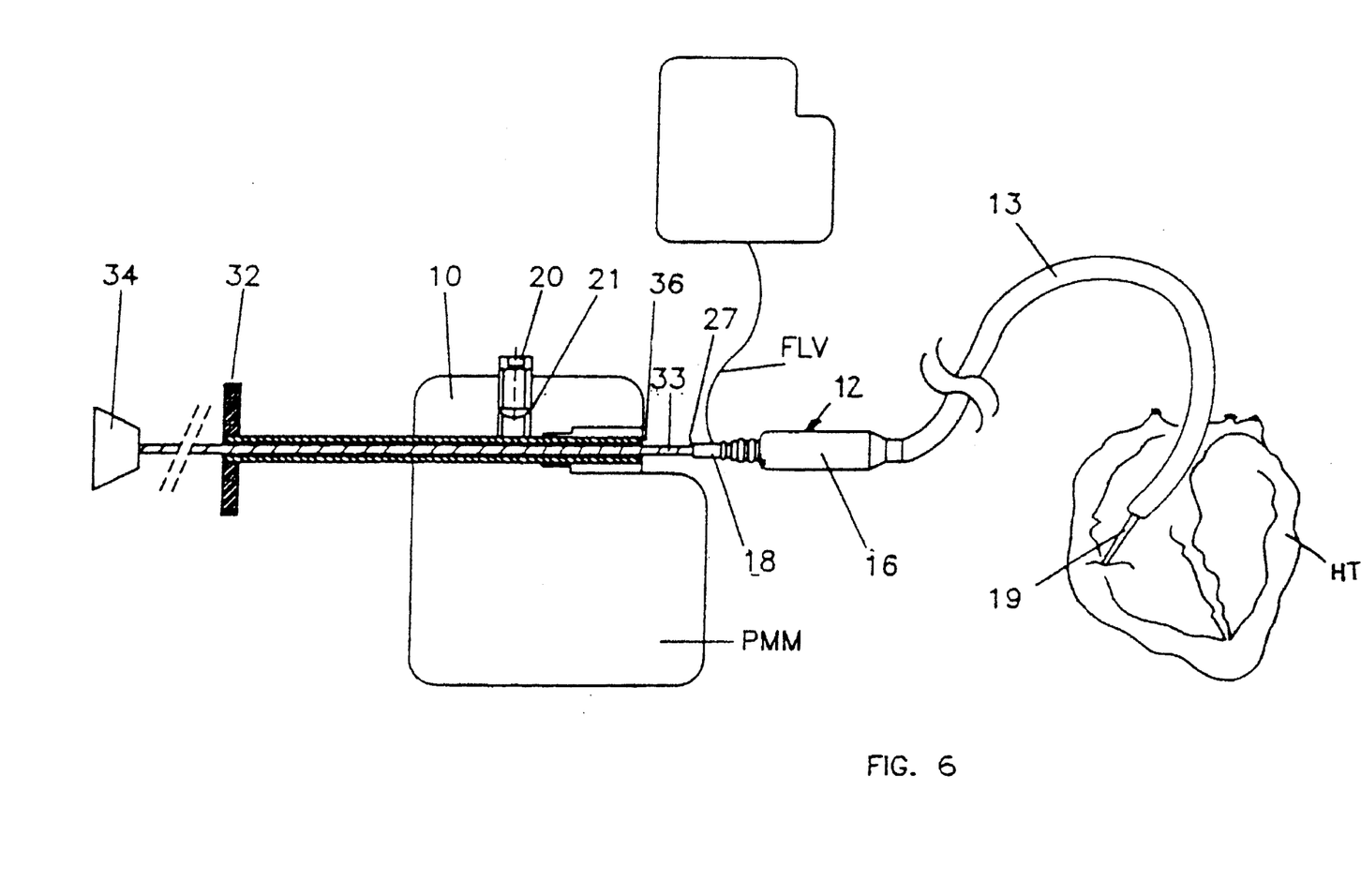
FIG. 6 is a similar section showing the tool completely inserted and the contact-pin expelled from the pacemaker, with the conducting wire still connected to the electrode-catheter.
Figure 8:
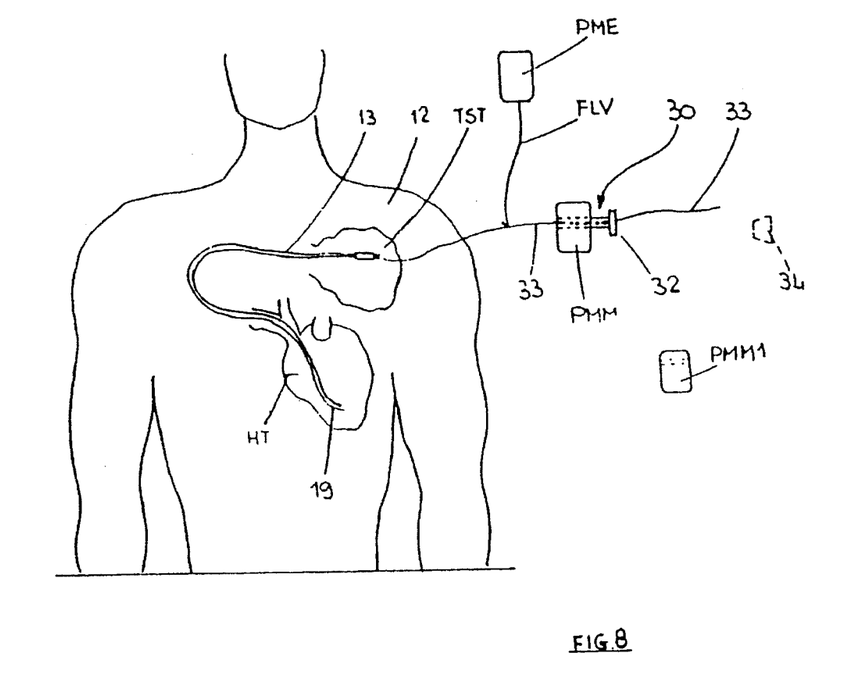
Figure 9:
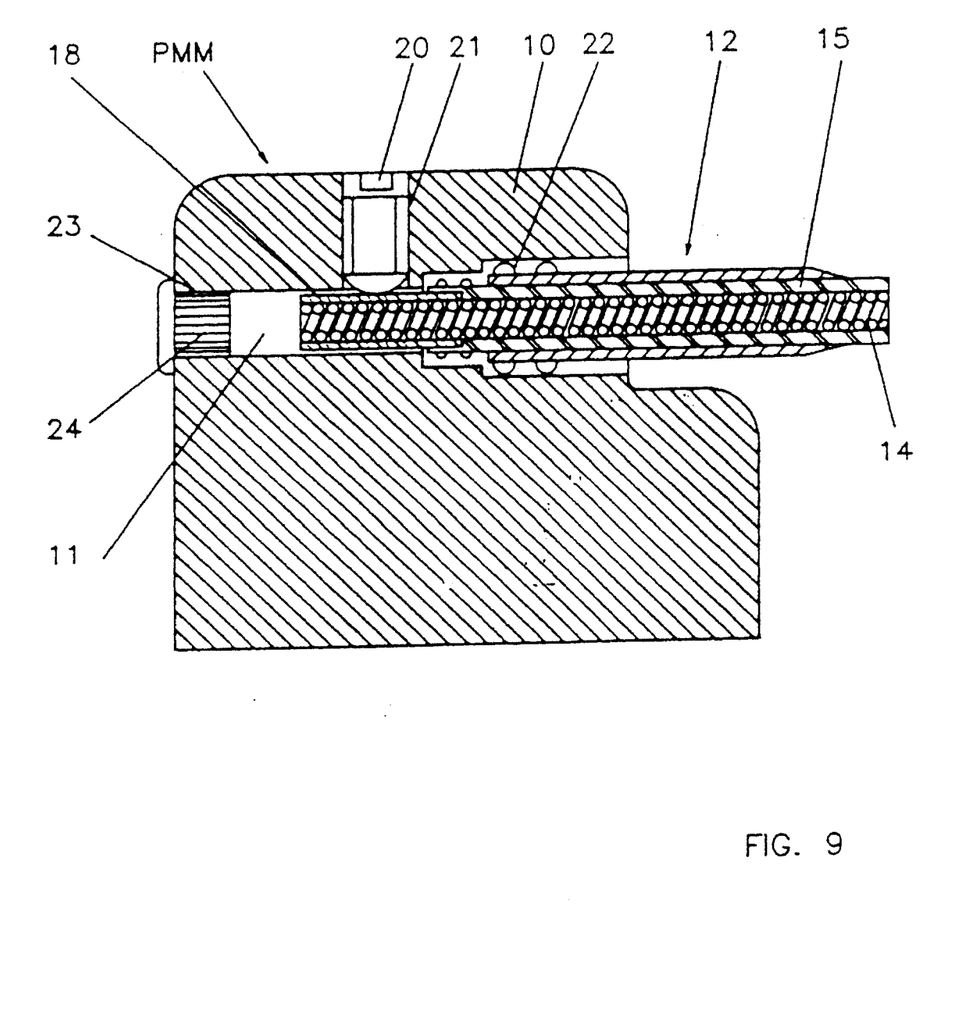
FIG. 9 is an enlarged section showing in detail the contact-pin of the electrode-catheter and its seat in the pacemaker, as modified according to the invention, for an electrode-catheter of the unipolar type.

Once the situation shown in FIG. 6 is reached, wherein contact-pin 12 has been removed from seat 11 through opening 22, temporary connection FLV is directly connected to contact tube 18, outside the pacemaker PMM being replaced; the latter and attached tool 30 can then slide along wire 33 until the situation shown in FIG. 8 is reached.

It can be noted that practically also during this stage electric stimulation of the heart HT is not interrupted as it is provided for by external pacemaker PME.

Therefore, it will be easy, by reversing the sequence of the above-described operations, to locate new pacemaker PMM1 (also of the improved type according to the invention) in pocket TST and fit contact-pin 12 into seat 11 without interrupting the electric stimulation of heart HT.

In particular, in passage 11 of new pacemaker PMM1, also of the modified type, another wire will be fitted and pushed inside spiral 14, from which the previously inserted wire 33 has been removed.

As an alternative, by making removable head 34 of the wire, the original wire could be left in place and utilized for this operation.

Once contact-pin 12 is fitted in pacemaker PMM1 just located in place in pocket TST, wire 33 will be removed, screw 20 will be tightened, opening 23 of passage 11 will be sealed with a "grommet" or plug 24 and pocket TST sutured.

Figure 10:
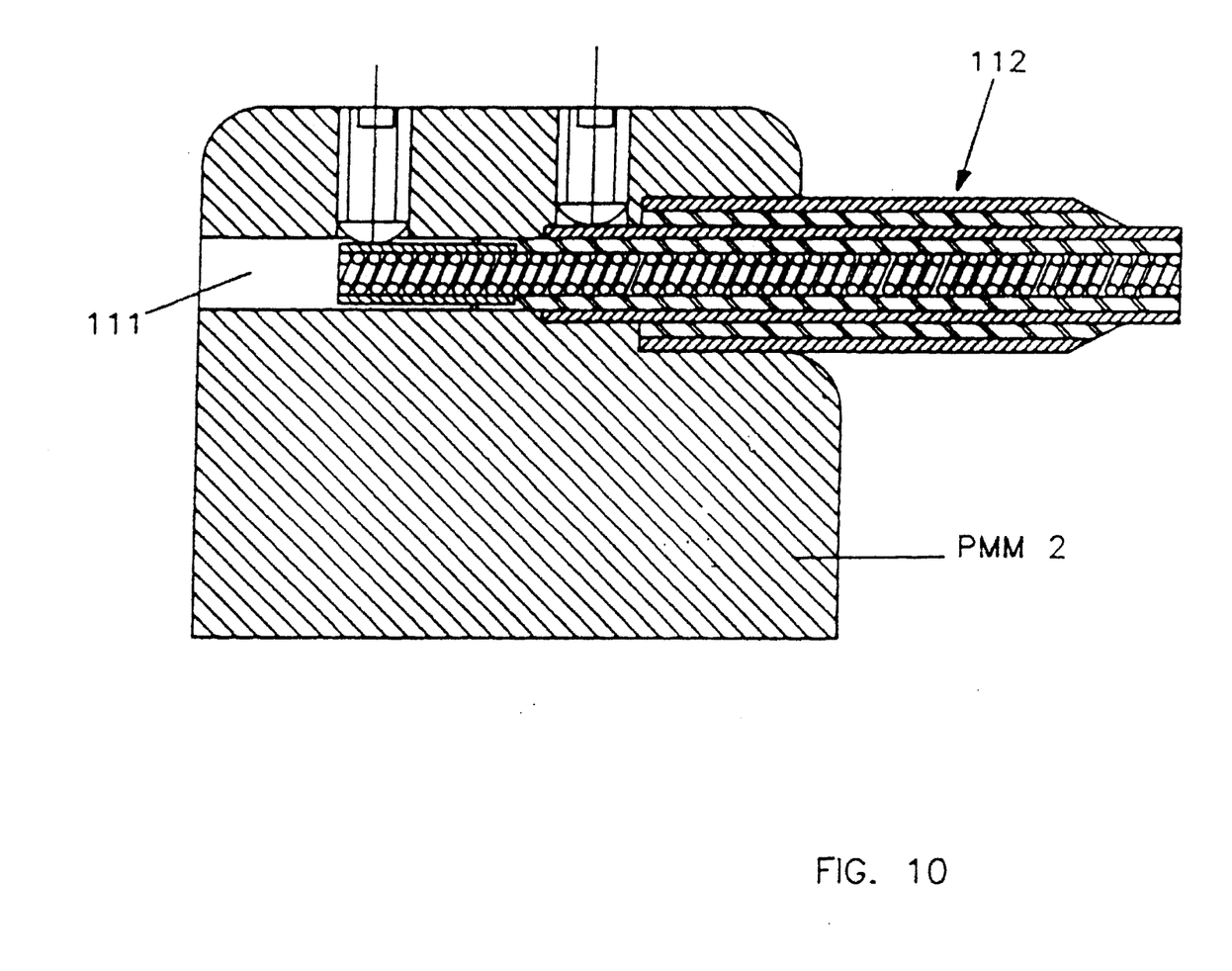
FIGS. 10 and 11 are similar sections related to a bipolar electrode-catheter and to a tripolar electrode-catheter, respectively.
Figure 11:
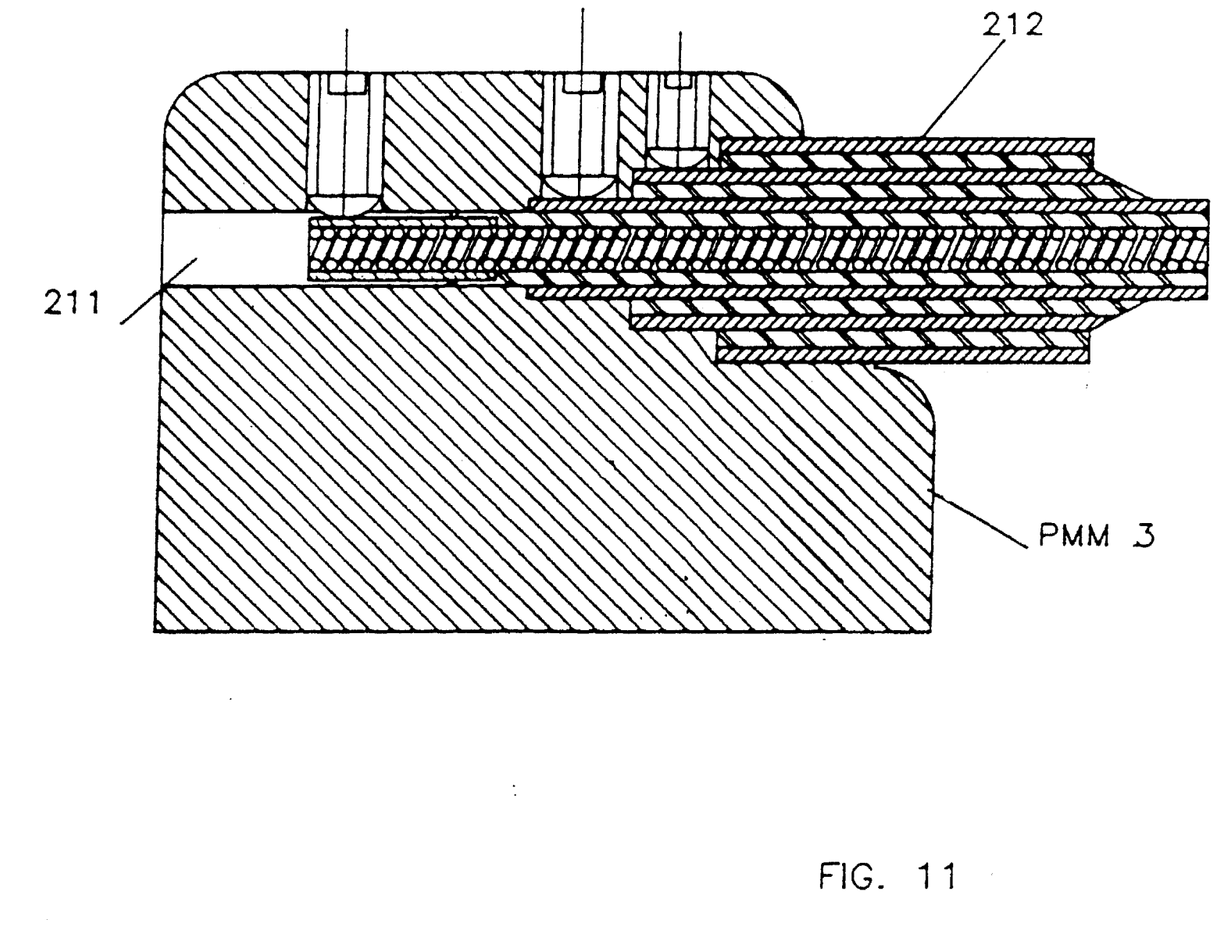

FIGS. 10 and 11, respectively, show in detail a pacemaker PMM2, also modified according to the invention, utilizing a bipolar electrode-catheter and a pacemaker PMM3 utilizing a tripolar electrode-catheter.

In practice, it can be noted that the improvement in the construction of this type of pacemakers regards only to the diameter of the passage accomodating the contact-pin, indicated by references 111, 118 and 211, 218 respectively; therefore, the tool to be used is totally identical to tool 30 described and illustrated in connection with FIGS. from 3 to 9.

I claim:

1. A pacemaker replacement system specially adapted to allow uninterrupted electric stimulation of a heart during pacemaker replacement comprising:

an electrode-catheter for stimulating the heart having a contact-pin with first and second contact-pin ends, the first contact-pin end comprising a contact tube and the second contact-pin end adapted to be inserted in the right ventricle of the heart, said electrode-catheter consisting of a helicoidal alloy spiral coated with an insulating sheath;

a first pacemaker being manufactured prior to initial use with a bore having first and second sides, the bore being open on the first and second sides, the first side being shaped to receive the contact-pin of the electrode-catheter, the second side being shaped to receive an elongated tool for pushing the contact-pin out of the first side o the bore and to provide access to the contact-pin when the contact-pin is seated in the bore of the first pacemaker, the first pacemaker having a locking screw extending into the bore for locking the contact-pin therein; and the elongated tool including a conducting element having first and second ends, the first end being shaped to fit in the second side of the bore in order to act on the contact-pin for pushing it out of the first side of the bore when necessary to replace the first pacemaker with a second pacemaker, the tool having sufficient longitudinal strength for pushing the contact-pin out of the first side of the bore, the first end being electrically conductive and shaped to maintain continuous electrical contact with the electrode-catheter when the tool is used to push the contact-pin out of the first side of the bore, and the second end being electrically conductive and shaped to allow electrical connection to an external pacemaker to continuously electrically stimulate the heart while the contact-pin is being pushed out of the first side of the bore.

2. The pacemaker replacement system of claim 1 wherein said second side of said bore is sealed with a removable plug.

3. The pacemaker replacement system of claim 1 wherein said elongated tool includes a cylindrical hollow body having a diameter and a connected handling head, the bore of the pacemaker having a diameter, and the diameter of said cylindrical body being essentially identical with the diameter of said bore of the pacemaker and said contact tube of said contact-pin so that, when said tool is inserted and pushed into said bore, it will expel said contact-pin from said bore by exerting a pushing action on said contact tube after said locking screw is unscrewed.

4. The pacemaker of claim 3 wherein the electrode catheter is a unipolar electrode-catheter.

5. The pacemaker of claim 3 wherein the electrode catheter is a multipolar electrode-catheter.

6. The pacemaker of claim 3 wherein said conducting element comprises a flexible metallic wire, equipped with a head and inserted in said cylindrical body, the flexible metallic wire having a diameter sufficiently small such that the flexible metallic wire may be pushed through the contact tube and, for a certain length, inside the spiral of said electrode-catheter in order to establish an optimal electric contact with said spiral, thus allowing stimulation signals provided by said external pacemaker connected thereto to reach the heart without any interruption.

7. The pacemaker of claim 6 wherein said head of said flexible metallic wire is removable.

8. A method of disconnecting an electrode-catheter from a first pacemaker to be replaced while providing uninterrupted electric stimulation of a heart comprising:

operating to obtain access to the first pacemaker to be replaced in a patient, the first pacemaker being connected to the electrode-catheter for stimulating the heart and the electrode-catheter having a contact-pin with a contact tube on one end and an other end adapted to be inserted in the heart, the electrode-catheter consisting of a helicoidal alloy spiral coated with an insulating sheath, the first pacemaker including a bore open on first and second sides, the first side being shaped to receive the contact-pin of the electrode-catheter, the second side being shaped to provide access to the contact-pin when the contact-pin is seated in the bore of the first pacemaker;

engaging an elongated tool having a conducting element with first and second ends in the second side of the bore in the first pacemaker so that the first end of the conducting element contacts the contact pin of the electrode-catheter;

connecting an external pacemaker to the second end of the conducting element;

disengaging the electrode-catheter from the first pacemaker by pushing the elongated tool into the second side of the bore to push the contact-pin out of the first side of the bore, while continuously maintaining connection between the electrode catheter and the external pacemaker through the conducting element of the elongated tool.

* * * * *

UNITED STATES PATENT AND TRADEMARK OFFICE
CERTIFICATE OF CORRECTION

PATENT NO. : 5,496,354
DATED : March 5, 1996
INVENTOR(S) : DeBellis

It is certified that error appears in the above-identified patent and that said Letters Patent is hereby corrected as shown below:

Column 2, Line 35: "electrode-catheter" should read - - electrode-catheter 13 - - .

Column 4, Line 25: "first side o" should read - - first side of - - .

Signed and Sealed this

Twenty-fifth Day of June, 1996

Attest:

BRUCE LEHMAN

*Attesting Officer*         *Commissioner of Patents and Trademarks*